United States Patent
Cho et al.

(10) Patent No.: US 11,975,190 B2
(45) Date of Patent: May 7, 2024

(54) SUPERIMPOSED WAVE MICROCURRENT APPLICATION DEVICE FOR LIVING BODY

(71) Applicant: NATURAL WELLTECH CO., LTD., Busan (KR)

(72) Inventors: Dong Shik Cho, Republic of Korea (KR); Shin Woo Cho, Busan (KR); Se Yeon Cho, Busan (KR)

(73) Assignee: NATURAL WELLTECH CO., LTD, Busan (KR)

( * ) Notice: Subject to any disclaimer, the term of this patent is extended or adjusted under 35 U.S.C. 154(b) by 453 days.

(21) Appl. No.: 17/285,454

(22) PCT Filed: Jan. 16, 2020

(86) PCT No.: PCT/KR2020/000823
§ 371 (c)(1),
(2) Date: Apr. 14, 2021

(87) PCT Pub. No.: WO2021/100970
PCT Pub. Date: May 27, 2021

(65) Prior Publication Data
US 2022/0118248 A1    Apr. 21, 2022

(30) Foreign Application Priority Data
Nov. 20, 2019   (KR) .................. 10-2019-0149269

(51) Int. Cl.
*A61N 1/22*   (2006.01)
*A61N 1/04*   (2006.01)
*A61N 1/20*   (2006.01)

(52) U.S. Cl.
CPC ............. *A61N 1/22* (2013.01); *A61N 1/0472* (2013.01); *A61N 1/205* (2013.01)

(58) Field of Classification Search
None
See application file for complete search history.

(56) References Cited

U.S. PATENT DOCUMENTS

2016/0184574 A1*  6/2016  Harris .................. A61N 1/0504
                                                          607/116
2020/0179697 A1*  6/2020  Schepis .............. A61N 1/36192

FOREIGN PATENT DOCUMENTS

KR    20000024420 A    5/2000
KR    100839675 B1     6/2008
(Continued)

OTHER PUBLICATIONS

International Search Report and Written Opinion for App. No. PCT/KR2020/000823, dated Aug. 18, 2020, 8 pages.

*Primary Examiner* — Michael W Kahelin
(74) *Attorney, Agent, or Firm* — Ferguson Case Orr Paterson

(57) ABSTRACT

The present invention promotes the activation of various physiological functions according to the stimulation of the body by superimposing a reference wave microcurrent of a low frequency and a main wave microcurrent of a high frequency into a preset pattern, or by additionally superimposing a multiple superimposed wave microcurrent discretely having a frequency of a larger magnitude sequentially than the main wave microcurrent and applying it to living organisms, and enables that the use and expandability can be increased by providing an additional configuration in which a multifunctional portable housing that can select AC electric stimulation and DC electric stimulation is worn on the wrist of the human body, thereby enabling the application of an electrical stimulation tailored to the body or disease/health condition of a user.

9 Claims, 18 Drawing Sheets

(56) References Cited

FOREIGN PATENT DOCUMENTS

| | | |
|---|---|---|
| KR | 20170010704 A | 2/2017 |
| KR | 101738673 B1 | 5/2017 |
| KR | 20170136901 A | 12/2017 |
| KR | 20180134514 A | 12/2018 |

* cited by examiner (a)

(b)

(a)

(b)

(c)

$$y(x,y) = y_m \sin(kx - wt)$$

- Displacement: $y(x,y)$
- Amplitude: $y_m$
- Phase: $(kx - wt)$
- Number of each wave: $k$
- Location: $x$
- Angular frequency: $w$
- Time: $t$

FIG. 12

SUPERIMPOSED WAVE MICROCURRENT APPLICATION DEVICE FOR LIVING BODY

BACKGROUND OF THE INVENTION

Technical Field

The present invention relates to a superimposed wave microcurrent applying device for living body that generates a microcurrent for stimulating a living body with an infiltration repetition frequency and applies it to objects such as plants, fish, livestock, poultry, humans, animals, and the like, more specifically, the reference wave microcurrent of a low frequency and the main wave microcurrent of a high frequency are superimposed into a preset pattern, or a multiple superimposed wave microcurrent discretely having a frequency of a larger magnitude sequentially than the main wave microcurrent is additionally superimposed and it is applied to living organisms, thereby promoting the activation of various physiological functions according to the stimulation of the living body, based on the structure of a smart watch or using a microcurrent output control application installed on a smart phone, it can be applied to various body parts including the wrist of the human body in various structures and methods, in particular, by detecting image information, iris characteristic information, vein characteristic information, and the like of the body part, the user's disease is estimated, and then a microcurrent tailored thereto is generated and outputted, thereby enabling the realization of the activation of physiological functions optimized for the current state of the user, in addition, when applied to plants, fish, livestock, and poultry, it helps to promote growth and increase immunity against infectious diseases by providing an additional configuration in which a multifunctional portable housing that can select AC electric stimulation and DC electric stimulation is worn on the wrist of the human body, thereby enabling the application of an electrical stimulation tailored to the body or disease/health condition of a user

BACKGROUND ART

In recent years, interest in health is gradually increasing against the backdrop of a rich material civilization. In addition, due to the change in dietary culture and the occurrence of various adult diseases due to lack of exercise, more attention has been paid to heatlth and accordingly, various functions and types of beauty-related devices have been developed and are widely used. Electrotherapy device is one of them.

Electrotherapy can be defined as a field of medical science that diagnoses and treats diseases using electricity such as direct current, current, pulsating current, and the like.

Types of electrotherapy include medical galvanism treatment, iontoporesis, electrical stimulation therapy (EST), transcutaneous electrical nerve stimulation (TENS), and functional electrical stimulation (FES), interferential current therapy (ICT), shortwave diathermy (SWD), microwave diathermy (MWD), ultrasound therapy, and the like.

Such, electric therapy has been used for treatment purposes such as musculoskeletal damage and disease, nervous system damage and disease, circulatory system disease, skin disease, internal medical disease, chronic inflammatory disease, and the like. The greatest advantage of such a treatment method using electronic energy is known as a therapy that uses the phenomena and characteristics of the body to cause electrical changes in the human body by electrical stimulation from the outside, which is useful for treatment.

However, electric therapy has a remarkable difference in its function depending on the frequency waveform, current, current intensity, application site, and the like.

In the conventional electrotherapy, it is common to deliver electrical stimulation to the body by supplying a regular low-frequency signal having the same frequency characteristics. However, since the low-frequency current is transmitted only through the patch-type electrode pad directly attached to the affected part of the patient, the range of transmission of electrical stimulation is narrow, therefore, it was somewhat inadequate to expect the therapeutic effect and massage effect through electrical stimulation, and since the electrical stimulation transmitted through the electrode pad is transmitted somewhat harder to the person to be treated, there is a problem in that the physical stimulation is transmitted to the person to be treated as it is.

DETAILED DESCRIPTION OF THE INVENTION

Technical Problem

Accordingly, the present invention improves the problems of the prior art, and aims to provide a new type of superimposed wave microcurrent applying device for living body, wherein the reference wave microcurrent that can have a very low frequency (VLF) range of 3 to 30 kHz and the main wave micro current that can have a long frequency (LF) range of 30 kHz to 300 kHz are superimposed into a preset pattern, or a multiple superimposed wave microcurrent discretely having a frequency of a larger magnitude sequentially than the main wave microcurrent is additionally superimposed and it is applied to living organisms such as plants, fish, livestock, poultry, humans, animals, and the like, to promote the activation of various physiological functions according to the stimulation of the living body, thereby activating various physiological functions according to the stimulation of the living body.

In addition, the present invention aims to provide a new type of superimposed wave microcurrent applying device for living body, wherein a reference wave microcurrent and a main wave microcurrent are generated in a way that the trajectory connecting the floor of the wave forming the main wave microcurrent becomes a waveform of the reference wave microcurrent, wherein the reference wave microcurrent is designed to respond to diseases such as pain, cancer, dementia, and viral infection through a structure having a waveform such as a triangle wave, a square wave, a sawtooth wave, a sine wave, and a DC wave including a staircase wave, or to allow the efficiency of body stimulation for helping the growth of the human body is to be increased, and meanwhile, to respond to diseases and viral infections of livestock and poultry such as plants grown in vinyl houses, greenhouses, and the like, fishes in farms and aquariums, and animals such as cattle, pigs, chickens, ducks, and the like, or to increase the biostimulation efficiency for animal growth activation.

In addition, the present invention aims to provide a new type of superimposed wave microcurrent applying device for living body capable of increasing the usability and scalability by providing a structure in which the microcurrent output device is driven by a microcurrent output control application installed in a smart watch or a smart phone that is integrated or separately disposed with the micro-current output device, thereby allowing to be applied to various body parts including the wrist part of the human body in various structures and methods In addition, the present invention aims to provide a new type of superimposed wave microcurrent applying device for living body capable of implementing activation of physiological functions optimized for the current state of the user by providing a structure in which image information, iris characteristic information, vein characteristic information, and the like of the body part are detected by a smart watch or smart phone to estimate the user's disease, and then a microcurrent tailored thereto is generated and outputted.

Technical Solution

According to a feature of the present invention for achieving the above object, the present invention provides a superimposed wave microcurrent applying device for living body characterized by consisting of a configuration comprising: a microcurrent generation unit 100 for biostimulation that generates a biostimulation microcurrent in which a reference wave microcurrent and a main wave microcurrent are superimposed; a microcurrent output unit 200 for biostimulation connected to the microcurrent generation unit 100 for biostimulation to receive the biostimulation microcurrent and outputs the biostimulation microcurrent to an external area to stimulate a subject live body in the external area; a controller 300 that controls the operation of the microcurrent generation unit 100 for biostimulation and the microcurrent output unit 200 for biostimulation wherein the microcurrent generation unit 100 generates a reference wave microcurrent having a frequency size belonging to a reference wave frequency range set as a very low frequency (VLF) wave of 3 to 30 kHz and a current value within the preset microcurrent value range for biostimulation, however, the reference wave microcurrent has any one waveform selected from a DC wave group including a triangular wave, a square wave, a sawtooth wave, a sine wave, and a step wave, wherein the reference wave microcurrent consists of a configuration that includes: a reference wave microcurrent generation module 110 that generates only in a region having a positive wave displacement value; and a main wave microcurrent generation module 120 that generates a frequency size within the main wave microcurrent frequency range set to a long wave (LF) of 30 kHz to 300 kHz, which is greater than the frequency size of the reference wave micro current, and a main wave microcurrent with a current value that falls within the set biostimulation microcurrent value range; and a microcurrent superimposing module 130 that superimposes the reference wave microcurrent and the main wave microcurrent, and wherein the main wave microcurrent generation module 120 generates a main wave microcurrent of the waveform that satisfies all of a first condition in which the wave displacement value of the main wave microcurrent for each time does not exceed the wave displacement value of the reference wave microcurrent at a corresponding time, and a second condition in which the wave displacement value of the main wave microcurrent by time and the wave displacement value of the reference wave microcurrent at a corresponding time are the same, and at the same time, generates a main wave microcurrent so that a trajectory connecting the floor of the wave constituting the main wave microcurrent becomes a waveform of the reference wave microcurrent.

Such a superimposed wave microcurrent applying device for living body according to the present invention may further include: a housing 400 that is worn on a human body and a body part of the animal; and a multiple superimposed wave microcurrent generation module 120' disposed inside the housing 400 wherein the microcurrent generation unit 100 for biostimulation discretely has a frequency of sequentially larger magnitude than the main wave microcurrent in the microcurrent generation unit 100 for biostimulation and microcurrent output unit for biostimulation, and generates one or more multiple superimposed wave microcurrent satisfying in the same pattern between microcurrent in which the first and second conditions satisfy the reference wave microcurrent and the main wave microcurrent are paired in order of frequency, wherein the microcurrent superposing module 130 may superimpose a main wave microcurrent, a multiple superimposed wave microcurrent, and a multiple superimposed wave paired with each other.

Such a superimposed wave microcurrent applying device for living body according to the present invention may further include: a housing 400 that is worn on a human body and a body part of the animal; a main board 500 disposed inside the housing 400 and on which the microcurrent generation unit 100 for biostimulation, the microcurrent output unit 200 for biostimulation, and the controller 300 are mounted in a chipset form; a control panel 600 that is formed to be exposed on the surface of the housing 400, receives a control signal according to a user's manipulation and transmits it to the controller 300, and receives and outputs information from the controller 300.

In such a superimposed wave microcurrent applying device for living body according to the present invention, the housing 400 consists of a configuration that includes: a watch-type main body block 410 made of a block body shape having a preset thickness corresponding to the shape of a main watch body, and a center portion of the bottom surface in contact with the living body consists of an AC electric stimulation plate 430a; and a connection band 420 connected to both sides of the watch-type main body block 410 and fixed to the wrist area of a human body, wherein the AC electric stimulation plate 430a is connected to the microcurrent output unit 200 for biostimulation to receive the microcurrent for biostimulation.

Here, the watch-type body block 410 of the housing 400 additionally forms a DC electric stimulation electrode 430b at the edge of the bottom surface in contact with a living body, and the DC electric stimulation electrode 430b may be connected to a DC power generator 450 disposed inside the housing 400 to receive a DC current for biostimulation.

In such a superimposed wave microcurrent applying device for living body according to the present invention, the connection band 420 may be attached with a biostimulatory mineral body 700 including germanium and crystal in an area to be in contact with a living body.

Such a superimposed wave microcurrent applying device for living body according to the present invention is characterized by including any one or more selected from the group of: a microcurrent output terminal 1 provided with the microcurrent generation unit 100 for biostimulation and the microcurrent output unit 200 for biostimulation; a smart watch 2 made in the shape of a wristwatch, worn on the user's wrist, and equipped with the controller 300, and a DB 2a in which the microcurrent setting information for generating the microcurrent for the biostimulation is databased; a user portable communication terminal 3, carried by a user for mobile communication, installed with a microcurrent output control application 4 interlocked with the controller 300, wherein the microcurrent output control application 4 includes a DB 2a in which the microcurrent setting information for generating the microcurrent for the biostimulation is databased, wherein the smart watch 2 is any one selected from: an output terminal integrated smart watch in which the smart watch 2 and the microcurrent output terminal 1 are integrated, and the controller 300 is built-in to perform direct control of the microcurrent output terminal 1; and an output terminal detachable smart watch separately provided from the microcurrent output terminal 1, and provided with a communication unit 2*b*, thereby transferring an output terminal operation control information to the micro-current output terminal 1 through wired or wireless communication with the microcurrent output terminal 1, and wherein the user portable communication terminal 3 is any one selected from: an indirect control communication terminal indirectly controlling the microcurrent output terminal 1 by transmitting the output terminal operation control information generated from the microcurrent output control application 4 to the smart watch 2 through wireless communication with the smart watch; and a direct control communication terminal directly controlling the microcurrent output terminal 1 by transmitting the output terminal operation control information generated from the microcurrent output control application 4 to the microcurrent output terminal 1 through wireless communication with the microcurrent output terminal 1 to the microcurrent output terminal 1.

In such a superimposed wave microcurrent applying device for living body according to the present invention, the microcurrent output terminal 1 can deliver microcurrent for biostimulation by being connected with: an wearable object for a user including a small sound device worn on the ear, glasses worn on the eyes, and a hat worn on the head; an object in contact with body of a user including a bed, a bed pad, and an electric pad.

In such a superimposed wave microcurrent applying device for living body according to the present invention, the output terminal integrated smart watch has a structure in which the smart watch 2 and the microcurrent output terminal 1 are detachably coupled, and in case of outputting a microcurrent for biostimulation to a living body area other than the wrist of a user, the microcurrent output terminal 1 is separated from the smart watch 2 and can be placed in a corresponding living body area.

In such a superimposed wave microcurrent applying device for living body according to the present invention, the microcurrent output terminal 1 is disposed on an area of a living body to detect current body information of a user, and any one selected from the smart watch 2 and the user portable communication terminal 3 may receive current body information of the user from the microcurrent output terminal 1 and generate and output monitoring information.

In such a superimposed wave microcurrent applying device for living body according to the present invention, any one or more selected among the group consists of: a solar cell 5 disposed on the surface of the smart watch 2 to generate power by receiving sunlight; a body temperature charging unit 6 that generates power from body temperature transmitted from the wrist where the smart watch 2 is disposed; a wireless wave charging unit 7 for producing power from wireless waves including radio waves for Wi-Fi communication, radio waves for Bluetooth communication, and radio waves for LTE communication received by the smart watch 2; and a vibration charging unit 8 for generating power from shaking motion of the smart watch may be provided in the smart watch 2.

In such a superimposed wave microcurrent applying device for living body according to the present invention, any one selected from the smart watch 2 and the user portable communication terminal 3, may be provided with any one or more selected among a group consists of: a body image information detector 9 for generating image information of a body part used for disease diagnosis; an iris recognition sensor 10 for detecting iris characteristic information of a user; a vein recognition sensor 11 for detecting vein characteristic information of a user, wherein any one selected from a human body diagnosis unit 12 provided in the smart watch 2 and the microcurrent output control application 4 provided in the user portable communication terminal 3 estimates disease of a user from information inputted from any one or more selected among a group consists of the body image information detector 9, the iris recognition sensor 10, and the vein recognition sensor 11, and wherein the smart watch 2 and the microcurrent output control application 4 receive microcurrent setting information corresponding to the estimated disease of a user from the DB 2*a*, generate output terminal operation control information, and then it may be transmitted to the microcurrent output terminal 1.

Meanwhile, a superimposed wave microcurrent applying device for living body according to the present invention applied to human bodies and animals may further include: a fixed frame 800 disposed in the plant cultivation area, wherein a plurality of microcurrent output units 200 for biostimulation are spaced apart and fixed; a solar panel 900 installed at a set point to perform solar power generation; a power supply device 1000 receiving and storing power from the solar panel 900; a microcurrent generation unit large-capacity casing 1100 installed at a set point, connected to the power supply 1000 and a public power supply to receive power, and wherein a plurality of microcurrent generation units 100 for biostimulation are integrated; and a plurality of connection cables 1200 connecting the microcurrent generation unit large-capacity casing 1100 and a plurality of microcurrent output units 200 for biostimulation.

A superimposed wave microcurrent applying device for living body according to the present invention applied to fish may further include: a fixed frame 800 disposed in a fish farming area, in which at least one microcurrent output unit 200 for biostimulation is spaced apart and fixed, and each microcurrent output unit 200 for biostimulation is installed so as to be in contact with a tank 1300 of the fish farming area; a solar panel 900 installed at a set point to perform solar power generation; a power supply device 1000 receiving and storing power from the solar panel 900; a microcurrent generation unit large-capacity casing 1100 installed at a set point, connected to the power supply 1000 and a public power supply to receive power, and integrated with a plurality of microcurrent generation units 100 for biostimulation; and a plurality of connection cables 1200 connecting the microcurrent generation unit large-capacity casing 1100 and one or more microcurrent output units 200 for biostimulation.

A superimposed wave microcurrent applying device for living body according to the present invention applied to livestock and poultry may further include: a solar panel 900 installed at a set point in an animal breeding area where livestock and poultry are reared to perform solar power generation; a power supply device 1000 receiving and storing power from the solar panel 900; a microcurrent generation unit large-capacity casing 1100 installed at a set point, connected to the power supply 1000 and a public power supply to receive power, and integrated with a plurality of microcurrent generation units 100 for biostimulation; and a plurality of connection cables 1200 connecting the microcurrent generation unit large-capacity casing 1100 and a plurality of microcurrent output units 200 for biostimulation attached to the breeding house 1400 of the animal breeding area.

Advantageous Effects of Invention

According to a superimposed wave microcurrent applying device for living body, there is an effect of activating various physiological functions according to the stimulation of the living body since the reference wave microcurrent that can have a very low frequency (VLF) range of 3 to 30 kHz and the main wave micro current that can have a long frequency (LF) range of 30 kHz to 300 kHz are superimposed into a preset pattern, or a superimposed wave microcurrent discretely having a frequency of a larger magnitude sequentially than the main wave microcurrent is additionally superimposed and it is applied to living organisms such as plants, fish, livestock, poultry, humans, animals, and the like.

In addition, according to a superimposed wave microcurrent applying device for living body, a reference wave microcurrent and a main wave microcurrent are generated in a way that the trajectory connecting the floor of the wave forming the main wave microcurrent becomes a waveform of the reference wave microcurrent, and since the reference wave microcurrent is generated to have a waveform such as a triangle wave, a square wave, a sawtooth wave, a sine wave, and a DC wave including a staircase wave, there is an effect in that the efficiency of body stimulation for responding to diseases such as pain, cancer, dementia, and viral infection or helping the growth of the human body is to be increased, and meanwhile, to respond to diseases and viral infections of livestock and poultry such as plants grown in vinyl houses, greenhouses, and the like, fish in farms and aquariums, and animals such as cattle, pigs, chickens, ducks, and the like, or to increase the biostimulation efficiency for animal growth activation. In particular, by applying the superimposed wave microcurrent applying device for living body of the present invention to a cultured animal, the possibility of replacing antibiotics arises, and it can be used to treat wounds in animals as well.

In addition, according to a superimposed wave microcurrent applying device for living body according to the present invention, since the micro-current output is driven by a microcurrent output control application installed in a smart watch or smart phone that is integrated or separately disposed with the microcurrent output device, it can be applied to various body parts including the wrist part of the human body in various structures and methods, and accordingly, there is an effect of increasing the usability and expandability.

In addition, according to the superimposed wave microcurrent applying device for living body according to the present invention, after disease of a user is estimated by detecting image information of a body area, iris characteristic information, vein characteristic information, and the like by a smart watch or smartphone, and then a structure in which a microcurrent tailored to this is generated and outputted is provided, so there is an effect of activating physiological functions optimized for the current state of the user.

BRIEF DESCRIPTION OF THE DRAWINGS

FIG. 12 is an exemplary diagram of a displacement value function of a reference wave microcurrent and a main wave microcurrent according to an embodiment of the present invention;

DETAILED DESCRIPTION OF EMBODIMENTS

Figure 1:
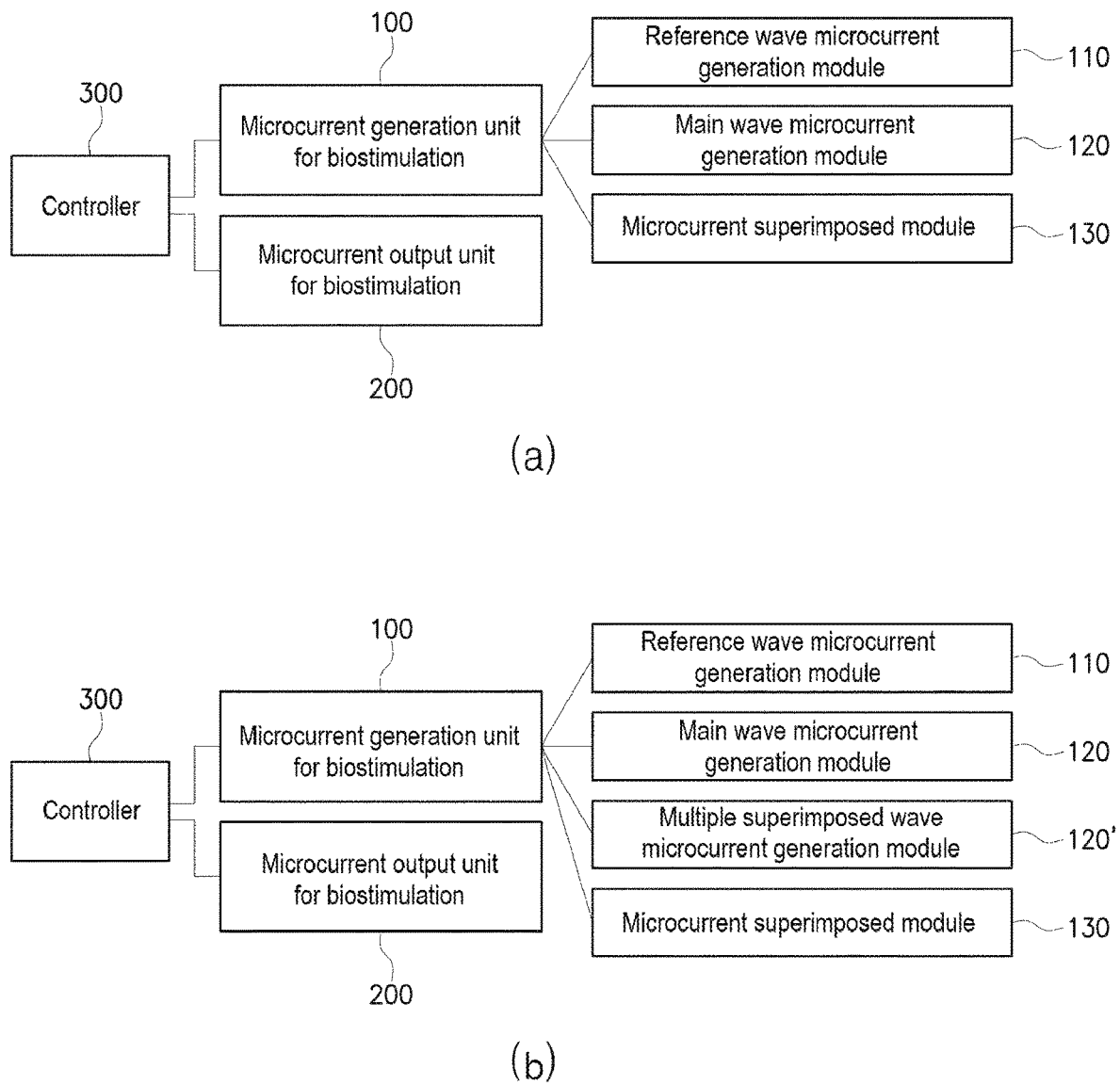
FIG. 1(*a*) and FIG. 1(*b*) are block diagrams of a superimposed wave microcurrent applying device for living body according to the present invention.

Hereinafter, an embodiment of the present invention will be described in detail with reference to FIGS. 1 to 18 in the accompanying drawings. Meanwhile, in the drawings and detailed description, the illustrations and mentions of structures and functions that can be easily understood by those in the field such as general microcurrent, biostimulation by microcurrent, superposition of waves, theater wave (VLF), long wave (LF), triangle wave, square wave, sawtooth wave, staircase wave, chipset, control panel, germanium, Crystal, bio-irritating minerals, solar panel, power supply, connection cable, smart watch, application, solar cell, body temperature charging technology, wireless wave charging technology, vibration charging technology, iris recognition technology, vein recognition technology, and the like have been simplified or omitted. In particular, in the illustration and detailed description of the drawings, detailed description and illustration of the specific technical configuration and operation of elements not directly related to the technical features of the present invention will be omitted, and only the technical configuration related to the present invention has been briefly illustrated or described.

A superimposed wave microcurrent applying device for living body according to the present invention consists of a configuration including a microcurrent generation unit 100 for biostimulation, a microcurrent output unit 200 for biostimulation, and a controller 300 as shown in FIG. 1.

The microcurrent generation unit 100 for biostimulation is a unit that generates microcurrent for biostimulation by superimposing reference wave microcurrent and main wave microcurrent.

Here, the microcurrent generation unit 100 according to the embodiment of the present invention includes a reference wave microcurrent generating module 110, a main wave microcurrent generating module 120, and a microcurrent superimposing module 130.

Figure 11:
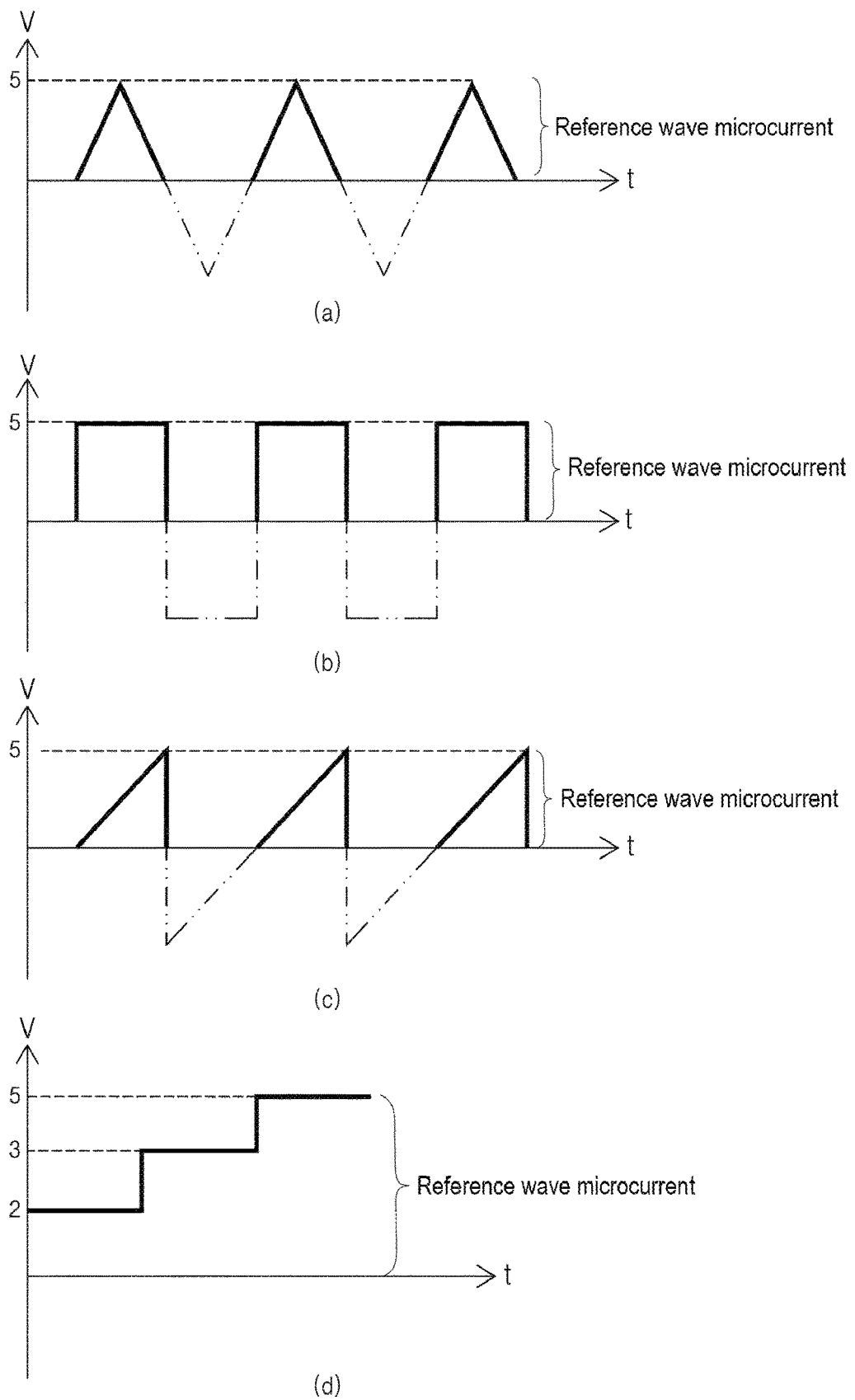
FIGS. 11(*a*) to 11(*d*) are exemplary waveforms of reference wave microcurrent according to an embodiment of the present invention.

The reference wave microcurrent generation module 110 is a module that generates a reference wave microcurrent having a frequency size within the reference wave frequency range set as a very low frequency (VLF) of 3 to 30 kHz and a current value within the set microcurrent value range for biostimulation. The reference wave microcurrent has a waveform such as a triangular wave, a square wave, a sawtooth wave, a sine wave, and a step wave as shown in FIGS. 11(*a*) to 11(*d*), and in particular, the reference wave microcurrent generation module 110 according to an embodiment of the present invention allows the reference wave microcurrent to be generated only in a region having a positive wave displacement value.

Figure 13:
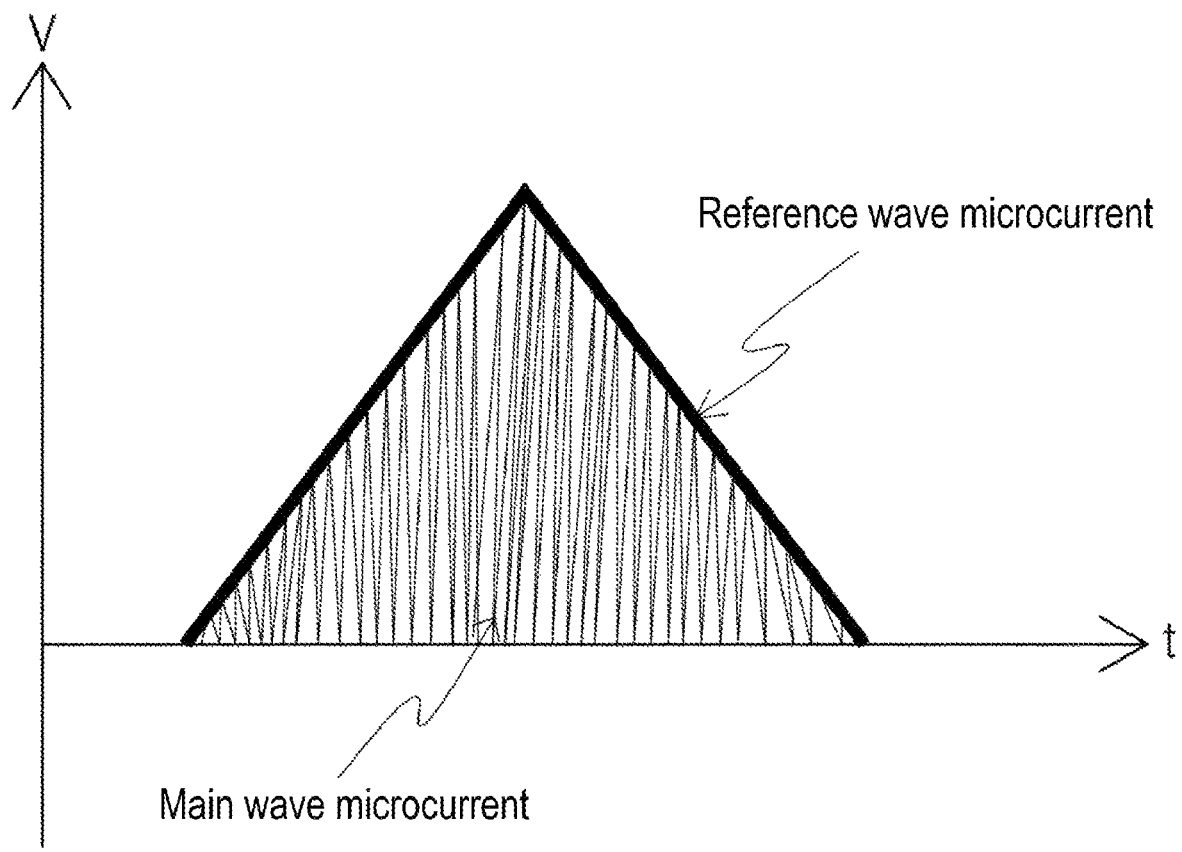
FIG. 13 is a view showing that a main wave micro current is generated in response to a waveform of a reference wave micro current in a main wave micro current generation module according to an embodiment of the present invention.
Figure 14:
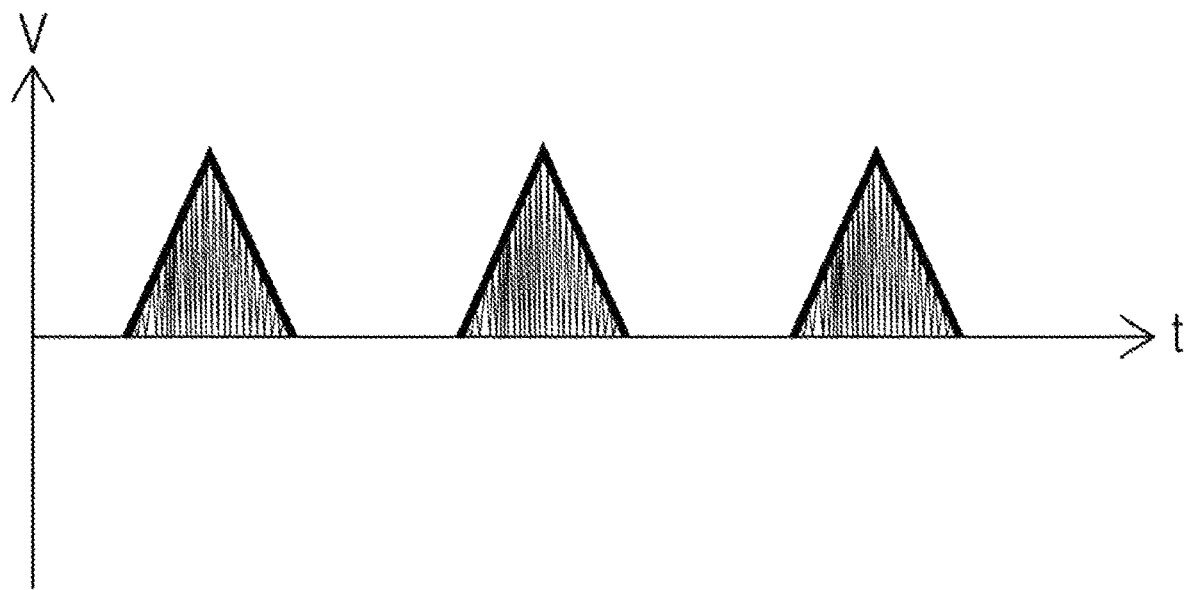
FIGS. 14 to 18 are exemplary diagrams of superposition of microcurrent in a microcurrent superimposition module according to an embodiment of the present invention.
Figure 15:
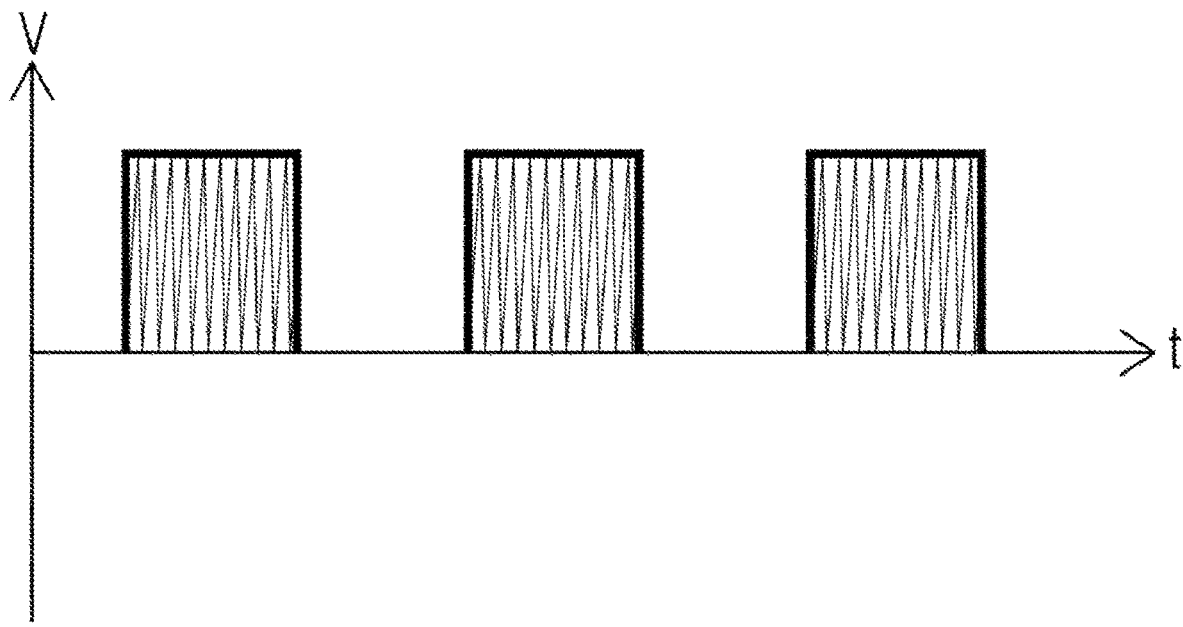
Figure 16:
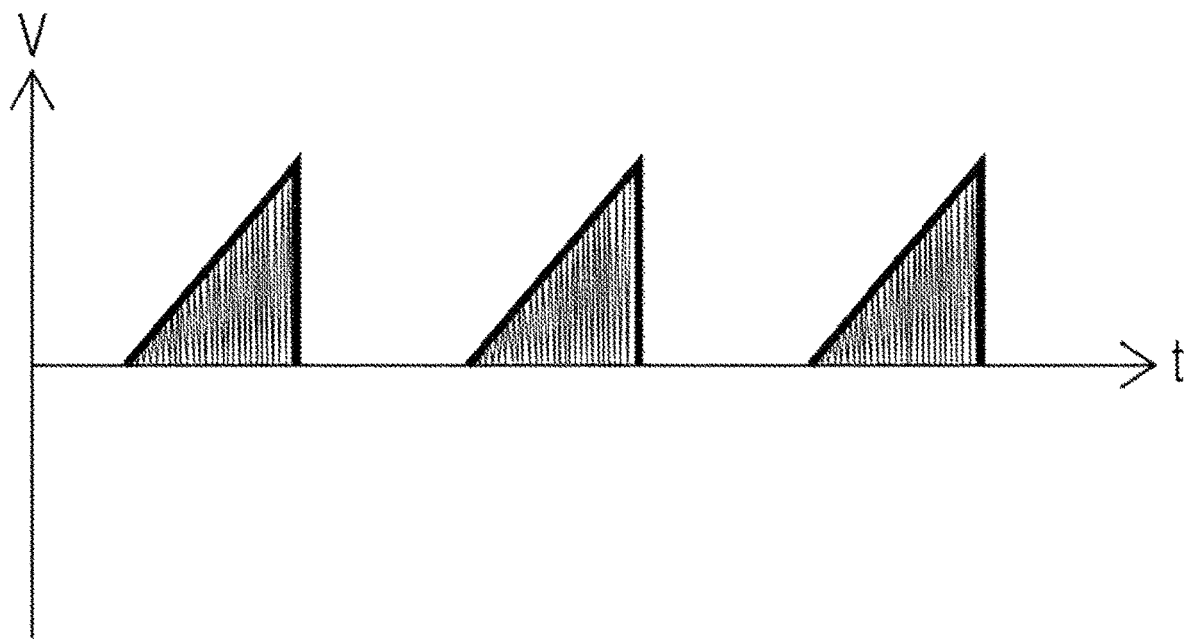
Figure 17:
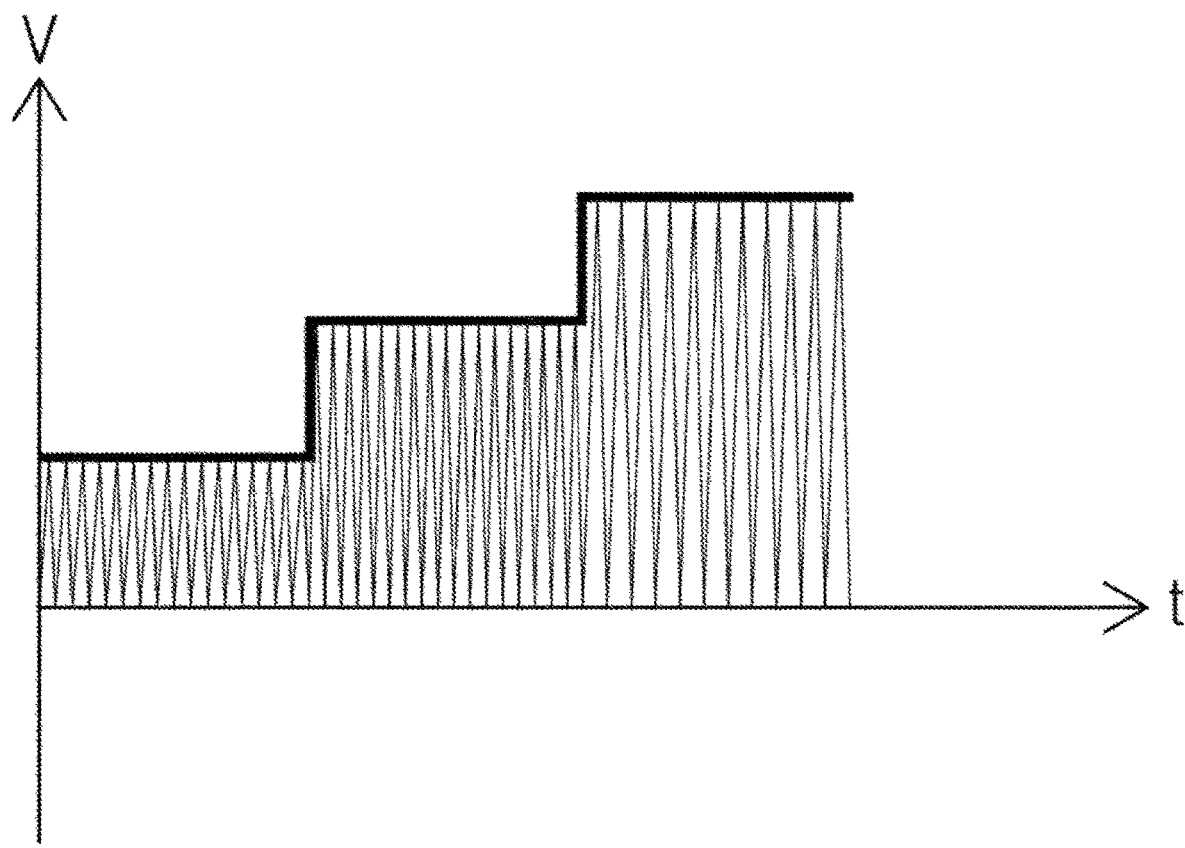

The main wave microcurrent generation module 120 is a module in which a main wave microcurrent having a frequency size belonging to the main wave microcurrent frequency range set to a low frequency (LF) of 30 kHz to 300 kHz, which is larger than the frequency size of the reference wave microcurrent, and a current value that falls within the set biostimulation microcurrent value range are generated. Here, the main wave microcurrent generation module 120 according to an embodiment of the present invention generates a main wave microcurrent of the waveform that satisfies all of the first condition that the wave displacement value of the main wave microcurrent by time does not exceed the wave displacement value of the reference wave microcurrent at that time, and the second condition in which the sign of the wave displacement value of the main wave microcurrent by time and the wave displacement value of the reference wave microcurrent at that time are the same (Refer to the displacement value function of the reference wave microcurrent and the main wave microcurrent in FIG. 12). And the main wave microcurrent generation module 120 according to an embodiment of the present invention generates a main wave microcurrent in a way that the trajectory connecting the floor of the wave forming the main wave microcurrent becomes the waveform of the reference wave microcurrent as shown in FIG. 13.

The microcurrent superimposing module 130 is a module that superimposes the reference wave microcurrent and the main wave microcurrent. The microcurrent superimposition module 130 according to an embodiment of the present invention superimpose the reference wave microcurrent and the main wave microcurrent as a structure in which the main wave microcurrent periodically vibrates inside the waveform of the reference wave microcurrent as shown in FIGS. 14 to 17.

Figure 18:
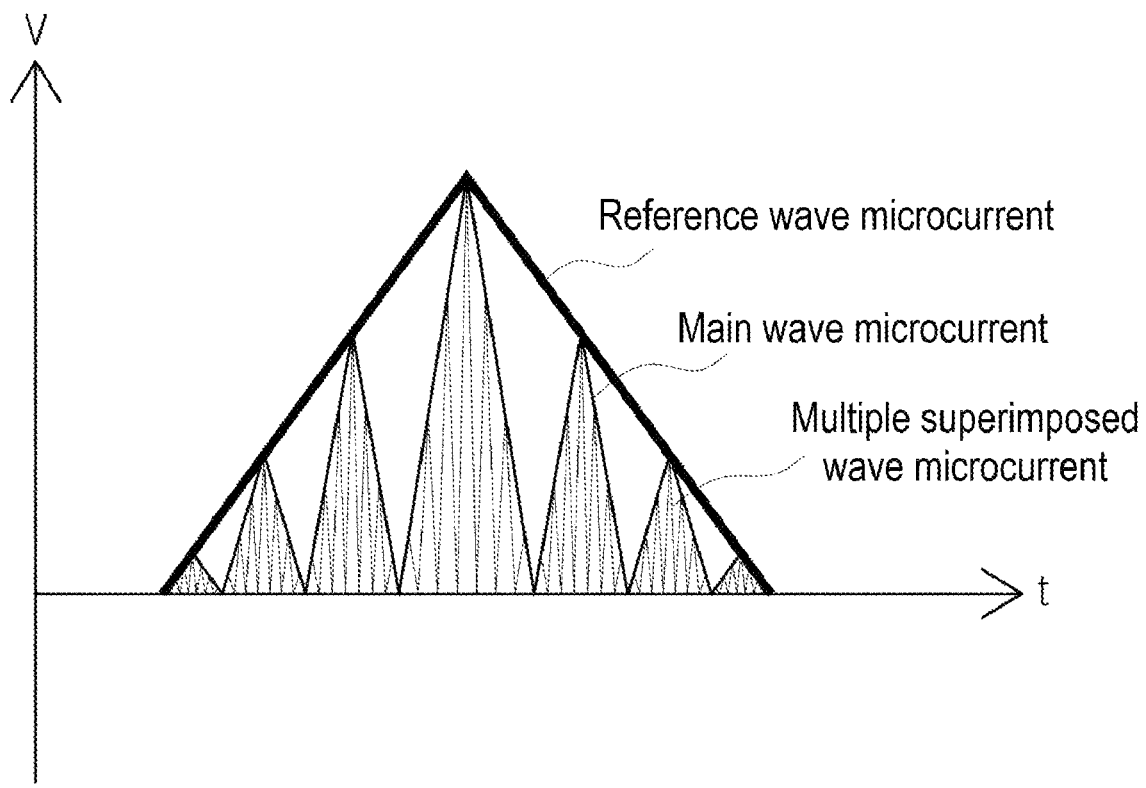

Meanwhile, the microcurrent generation unit 100 for biostimulation may additionally include a multiple superimposed wave microcurrent generation module 120' as shown in FIG. 1(*b*), and the multiple superimposed wave microcurrent generation module 120' is a module discretely having a frequency of sequentially larger magnitude than the main wave microcurrent as shown in FIG. 18, and generating one or more microcurrents for multiple superimposing that satisfy the same pattern between the first condition and the second condition, which are satisfied by the reference wave microcurrent and the main wave microcurrent, are paired in order of the magnitude of the frequency.

In response to this, the microcurrent superimposed module 130 superimposes the main wave microcurrent and multiple superimposed wave microcurrents paired with each other, and multiple superimposed wave paired with each other.

The microcurrent output unit 200 for biological stimulation is a unit connected to the microcurrent generation unit 100 for biostimulation to receive a microcurrent for biostimulation, and stimulates a subject living body in an external area by outputting the microcurrent for biostimulation in the corresponding external area.

The controller 300 controls the operation of the microcurrent generation unit 100 for biostimulation and the microcurrent output unit 200 for biostimulation.

Figure 2:
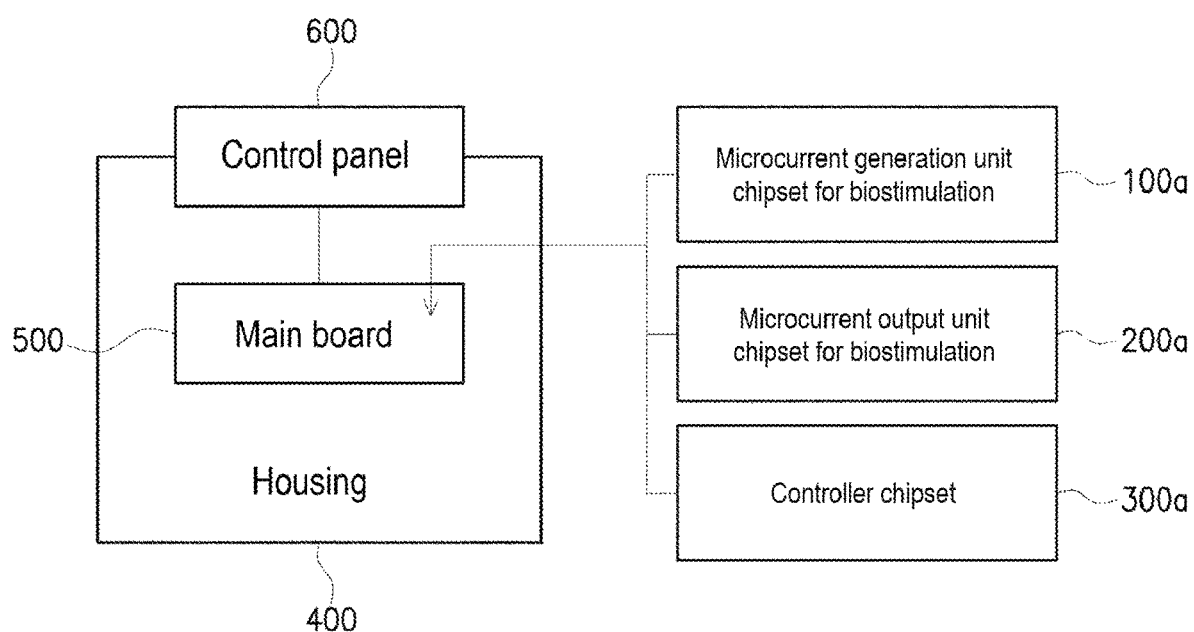
FIG. 2 is a block diagram of a superimposed wave microcurrent applying device for living body applied to human bodies and animals according to an embodiment of the present invention.

Here, the superimposed wave microcurrent applying device for living body according to the present invention can be applied to human bodies and animals, and to this end, the superimposed wave microcurrent applying device for living body according to an embodiment of the present invention may include a housing 400, a main substrate 500, and a control panel 600 as shown in FIG. 2.

The housing 400 is worn on a body area of a human body and an animal. In particular, the housing 400 that can be worn on a wrist of the human body includes a watch-type body block 410 and a connection band 420 as shown in FIGS. 3 and 4.

Figure 3:
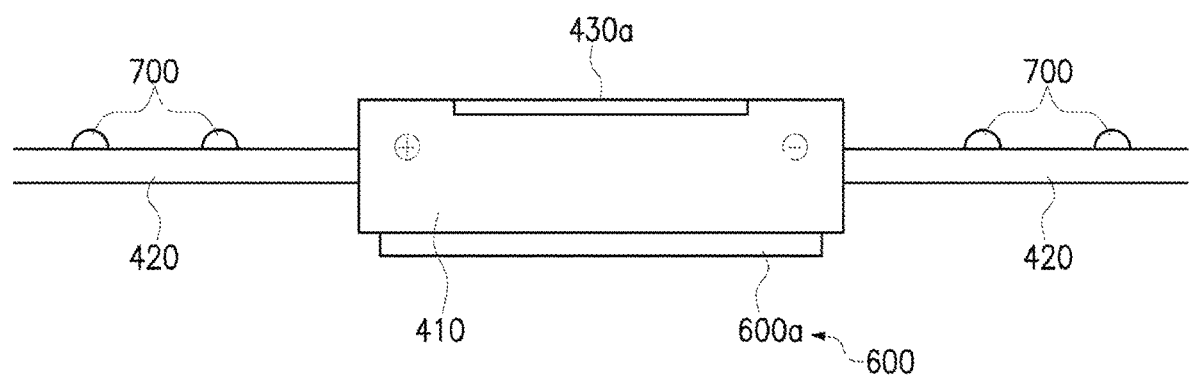
FIG. 3 is a view for showing a watch-type body having only an AC electric stimulation plate block according to an embodiment of the present invention.
Figure 4:
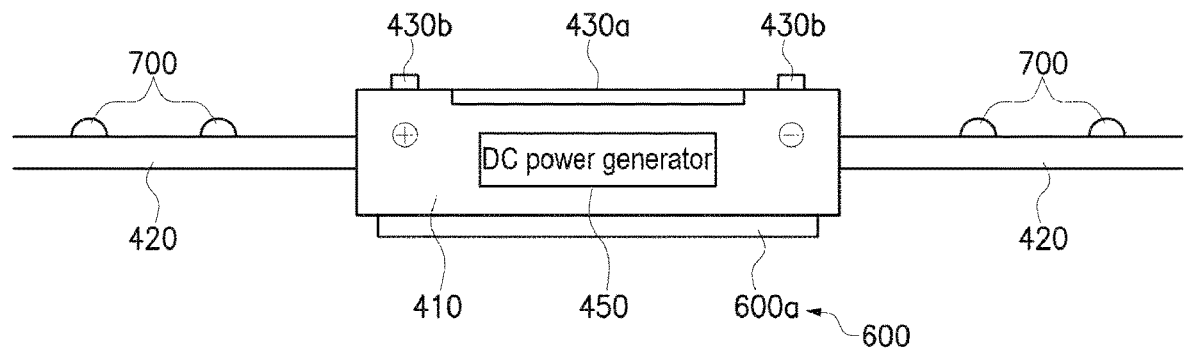
FIG. 4(*a*) and FIG. 4(*b*) are views for showing a watch-type body block additionally provided with an electrode for a DC electric stimulation according to an embodiment of the present invention.
Figure 4:
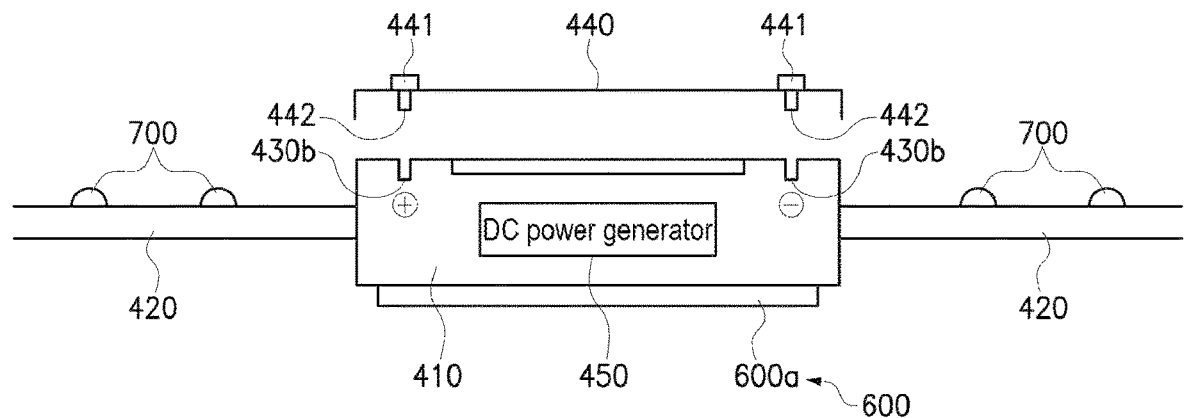

The watch-type body block 410 has a block body shape having a set thickness corresponding to the shape of the watch body, and as shown in FIG. 3, the central portion of the bottom surface in contact with the living body may be formed of an AC electrical stimulation plate 430*a*. In addition, as shown in FIG. 4, the watch-type main body block 410 may additionally form a DC electrical stimulation electrode 430*b* at an edge area of the bottom surface in contact with a living body.

The AC electric stimulation plate 430*a* may be formed in a circular plate shape. The DC electrical stimulation electrode 430*b* may be implemented as a pair of a positive (+) pole and a negative (−) pole. Here, the AC electrical stimulation plate 430*a* is connected to the microcurrent output unit 200 for biostimulation to receive the microcurrent for biostimulation, and the DC electrical stimulation electrode 430*b* is connected to a DC power generator 450 disposed inside the housing 400 to receive a direct current for biostimulation.

In addition, the DC electrical stimulation electrode 430*b* may be formed to protrude from the bottom surface of the watch-type body block 410 in contact with the living body as shown in FIG. 4*a*, in this case, when a user accidentally selects the DC electric stimulation function by mistake in selecting the AC electrical stimulation function/DC electric stimulation function, a sudden DC electric stimulation may be received. In response to this, the DC electrical stimulation electrode 430*b* may be concavely formed from the bottom surface of the watch-type main body block 410 in contact with the living body as shown in FIG. 4*b*. When the DC electrical stimulation electrode 430*b* is concavely formed from the bottom surface of the watch-type body block 410, a separate DC electrical stimulation plate 440 is coupled to the bottom surface of the watch-type body block 410 to be connected to the DC electrical stimulation electrode 430*b*, and thus direct current electrical stimulation can be smoothly transmitted to a living body contacting the bottom surface of the watch-type body block 410.

Here, the DC electric stimulation plate 440 protrudedly forms an electrical stimulation applying protrusion 441 on the outer side surface, and meanwhile, protrudedly forms an electrode connection protrusion 442 inserted into the concavely formed DC electric stimulation electrode 430*b* protrudes on the inner side surface.

The connection band 420 is connected to both sides of the watch-type body block 410 and fixed to the wrist of the human body, and the connection band 420 according to an embodiment of the present invention simultaneously performs biostimulation by a biostimulatory mineral object 700 by attaching the biostimulatory mineral 700 containing germanium and crystal to an area in contact with a living body.

The main board 500, disposed inside the housing 400, is mounted with a microcurrent generation unit chipset 100*a* for biostimulation, a microcurrent output unit chipset 200*a* for biostimulation, and a controller chipset 300*a*.

The control panel 600, exposed on the surface of the housing 400, receives a control signal according to the manipulation a user and transmits it to the controller 300, and receives information from the controller 300 and outputs. To this end, the control panel 600 may be formed of a touch screen 600*a*.

Figure 5:
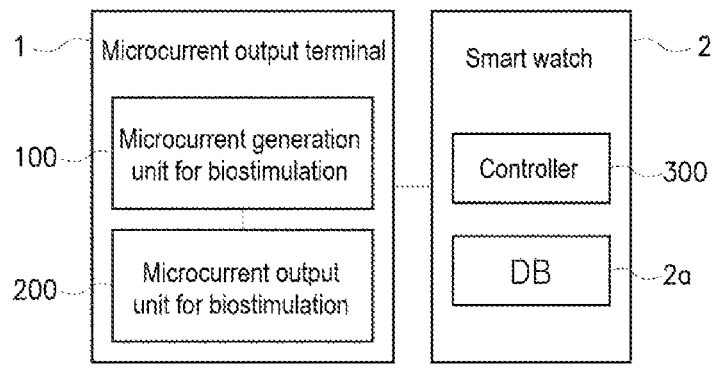
FIG. 5 is a superimposed wave microcurrent applying device for living body according to an embodiment of the present invention.
Figure 5:
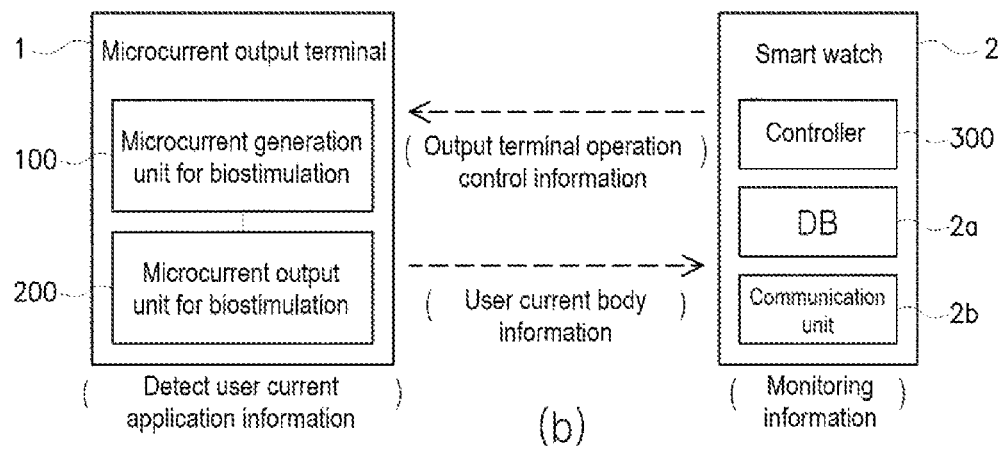
Figure 5:
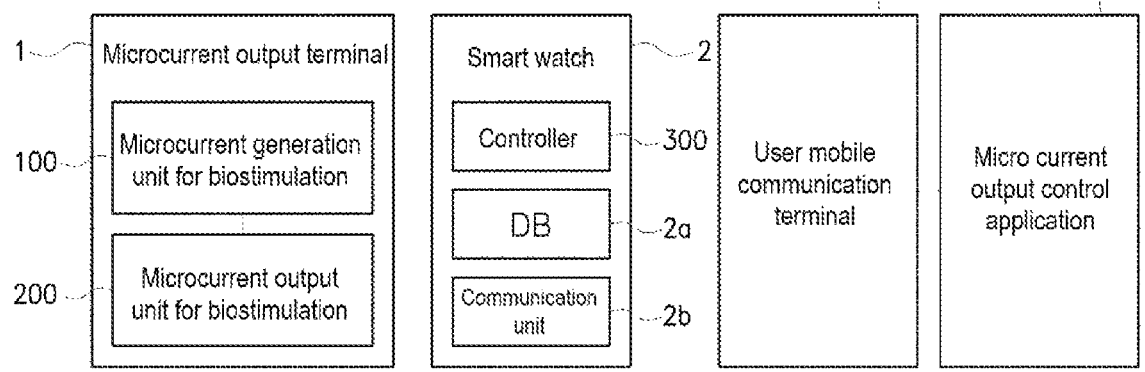

Meanwhile, the superimposed wave microcurrent applying device for living body according to the embodiment of the present invention being applied to the human body has a microcurrent output terminal 1 as a basic component as shown in FIG. 5, and a smart watch 2 or a user portable communication terminal 3 may be provided as an additional component.

The microcurrent output terminal 1 is provided with a microcurrent generation unit 100 for biostimulation and a microcurrent output unit 200 for biostimulation, and it is an element that is placed on an area of body of a user (wrist, wrist area, shoulder area, neck area, eyes area, face area, trunk area, leg area, foot area, and the like) to apply microcurrent for biostimulation to the corresponding body area. Such a microcurrent output terminal 1 can deliver microcurrent for biostimulation by being connected to a wearable object on a body of a user which may be a small sound device worn on the ears, glasses worn on the eyes, and a hat worn on the head. In addition, the microcurrent output terminal 1 may be connected to an object in contact with a body of a user, which may be a bed, a bed pad, or an electric pad, and may be used to deliver a microcurrent for biostimulation.

The smart watch 2 has a shape of a wrist watch and is worn on the wrist of a user, and includes a controller 300 and a DB 2*a*. Here, the DB 2*a* is a database in which microcurrent setting information for generating microcurrent for biostimulation is databased, and the microcurrent setting information can be set in conjunction with user characteristic information (gender, age, and the like) and can be set according to various types of user diseases.

The user portable communication terminal 3 is carried by a user to perform mobile communication, and a microcurrent output control application 4 interlocked with the controller 300 is installed. The controller 300 may be installed in the portable communication terminal 3 of a user, but unlike this, the controller 300 may be installed in the smart watch 2 or the microcurrent output terminal 1. In addition, the microcurrent output control application 4 includes a DB 2*a* in which microcurrent setting information for generating micro-current for biostimulation is databased.

Here, the smart watch 2 may be implemented as an integrated smart watch with an output terminal as shown in FIG. 5(*a*), or as a smart watch with a separate output terminal as in FIGS. 5(*b*) and 5(*c*).

The output terminal integrated smart watch is an integrated smart watch 2 and a microcurrent output terminal 1, the controller 300 is built into the smart watch 2 to directly control the microcurrent output terminal 1. Such an output terminal integrated smart watch may have a structure in which the smart watch 2 and the microcurrent output terminal 1 are detachably coupled, and when outputting microcurrent for biostimulation to biological areas other than the wrist of a user (eyes, wrists, shoulders, neck, face, trunk, legs, feet, and the like), the microcurrent output terminal 1 may be separated from the smart watch 2 and disposed in a corresponding body area.

The output terminal separate smart watch is provided separately from the microcurrent output terminal 1, and in this case, the smart watch 2 is provided with a communication unit 2*b* to transmit the output terminal operation control information to the microcurrent output terminal 1 through wired/wireless communication with the microcurrent output terminal 1.

The user portable communication terminal 3 may be implemented as an output terminal indirect control communication terminal or as an output terminal direct control communication terminal.

The output terminal indirect control communication terminal transmits the output terminal operation control information generated from the microcurrent output control application 4 to the smart watch 2 through wireless communication with the smart watch 2 to control the micro current output terminal 1 indirectly.

The output terminal direct control communication terminal transmits the output terminal operation control information generated from the microcurrent output control application 4 to the microcurrent output terminal 1 through wireless communication with the microcurrent output terminal 1 control the microcurrent output terminal 1 directly.

Meanwhile, the microcurrent output terminal 1 is disposed in an area of a living body to detect the current body information of a user, and in response to this, the smart watch 2 or the user portable communication terminal 3 may receive the current body information of the user from the microcurrent output terminal 1 to generate monitoring information and output.

Figure 6:
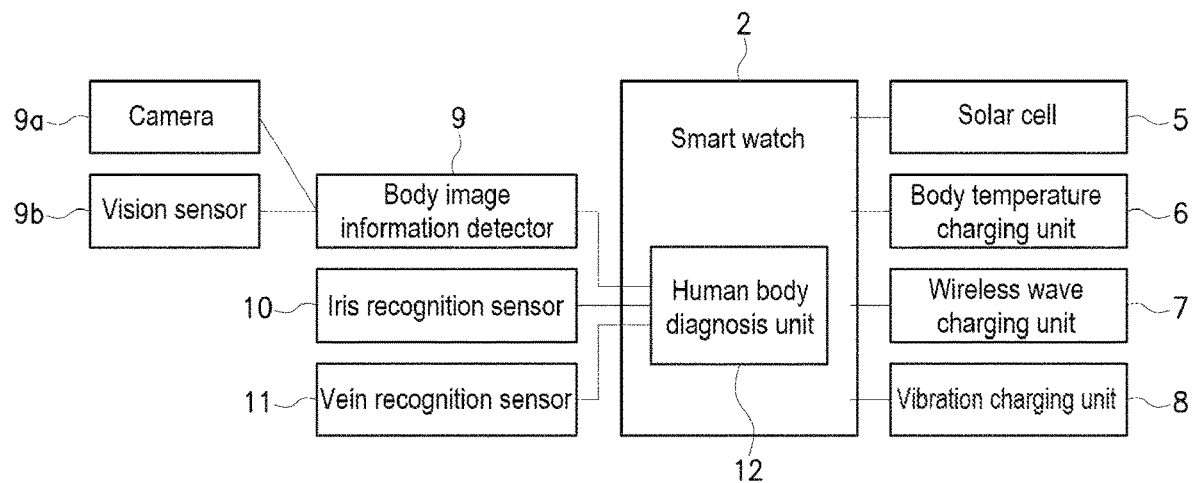
FIG. 6 is a superimposed wave microcurrent applying device for living body according to an embodiment of the present invention.

And the smart watch 2 is provided with a solar cell 5, a body temperature charging unit 6, a wireless wave charging unit 7, and a vibration charging unit 8 as shown in FIG. 6, and may be supplied with power through self-generation. Here, the solar cell 5 is disposed on the surface of the smart watch 2 and is irradiated with sunlight to produce power. The body temperature charging unit 6 produces power from body temperature delivered from the wrist where the smart watch 2 is disposed. The wireless wave charging unit 7 produces power from wireless radio waves including radio waves for Wi-Fi communication, radio waves for Bluetooth communication, and radio waves for LTE communication received by the smart watch 2. The vibration charging unit 8 produces power from the motion of shaking the smart watch 2.

Figure 7:
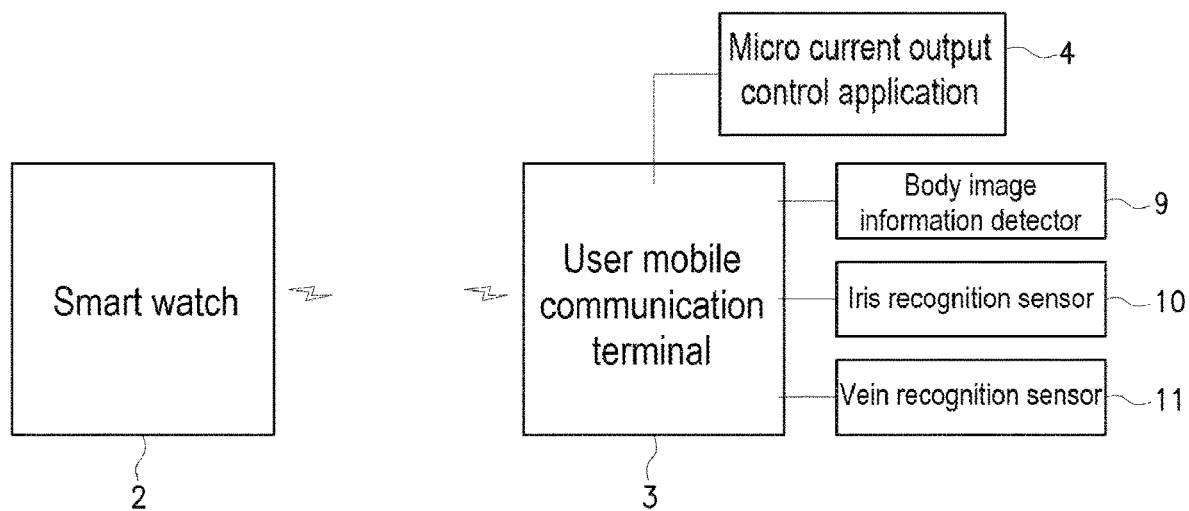
FIG. 7 is a superimposed wave microcurrent applying device for living body according to an embodiment of the present invention.

In addition, the smart watch 2 or the user portable communication terminal 3 includes a body image information detector 9, an iris recognition sensor 10, and a vein recognition sensor 11 as shown in FIGS. 6 and 7, and it is also possible to estimate user disease by detecting characteristic information.

The body image information detector 9 generates image information of a body part used for disease diagnosis, and may be formed of a camera 9a or a vision sensor 9b. Such a body image information detector 9 can perform dementia diagnosis through retinal imaging of the eyeball, or hair loss diagnosis through head area imaging, and various disease diagnosis through various body part imaging. The iris recognition sensor 10 detects iris characteristic information of a user, and may enable diagnosis of dementia, Parkinson's disease, diabetes, and the like. The vein recognition sensor 11 detects the vein characteristic information of a user, and may allow diagnosis of varicose veins or the like to be performed.

Here, the human body diagnosis unit 12 provided in the smart watch 2 and the microcurrent output control application 4 provided in the user portable communication terminal 3 estimates disease of a user from the information input from the body image information detector 9, the iris recognition sensor 10, the vein recognition sensor 11, and the smart watch 2 and the microcurrent output control application 4 receive the microcurrent setting information corresponding to the estimated user disease from the DB 2a to generate an output terminal operation control information, and then may transmit it to the microcurrent output terminal 1.

Figure 8:
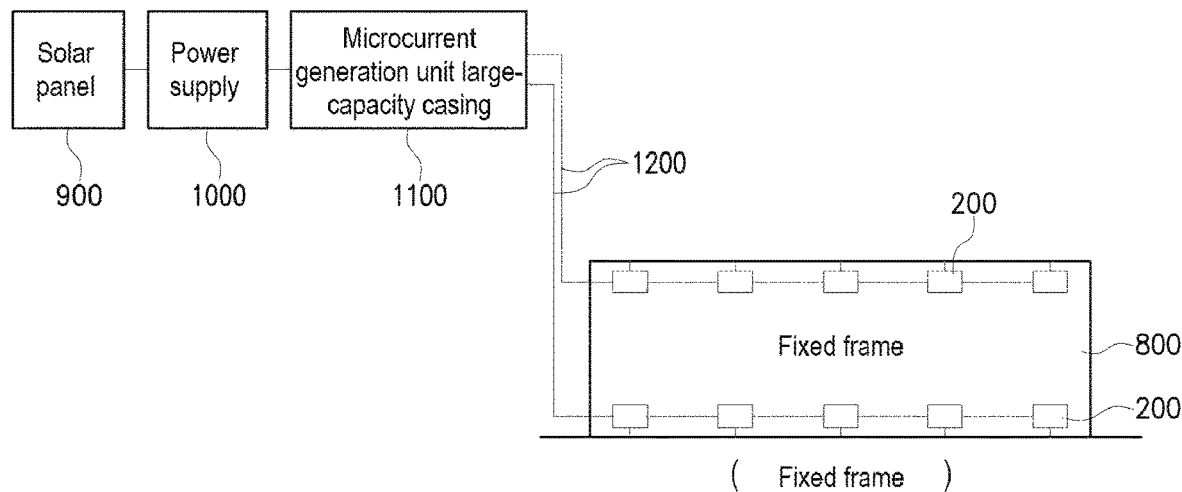
FIG. 8 is a view for showing a superimposed wave microcurrent applying device for living body applied to a plant according to an embodiment of the present invention.

The superimposed wave microcurrent applying device for living body according to the present invention can be applied to plants, and to this end, the superimposed wave microcurrent applying device for living body according to an embodiment of the present invention may be provided with a fixed frame 800, a solar panel 900, a power supply device 1000, a microcurrent generation unit large-capacity casing 1100, and a plurality of connection cables 1200 as shown in FIG. 8.

The fixed frame 800 is disposed in the plant cultivation area, and a plurality of microcurrent output units 200 for biostimulation are spaced apart and fixed.

The solar panel 900 is installed at a set point to perform solar power generation.

The power supply device 1000 receives and stores power from the solar panel 900.

The microcurrent generation unit large-capacity casing 1100 is installed at a set point and is connected to the power supply device 1000 and the public power supply to receive power. Since it is connected to a public power supply in preparation for a power outage, it is possible to stably receive power. A plurality of microcurrent generation units 100 for biostimulation are integrated in the microcurrent generation unit large-capacity casing 1100.

The plurality of connection cables 1200 are cables connecting the microcurrent generation unit large-capacity casing 1100 and the plurality of microcurrent output units 200 for biostimulation.

Figure 9:
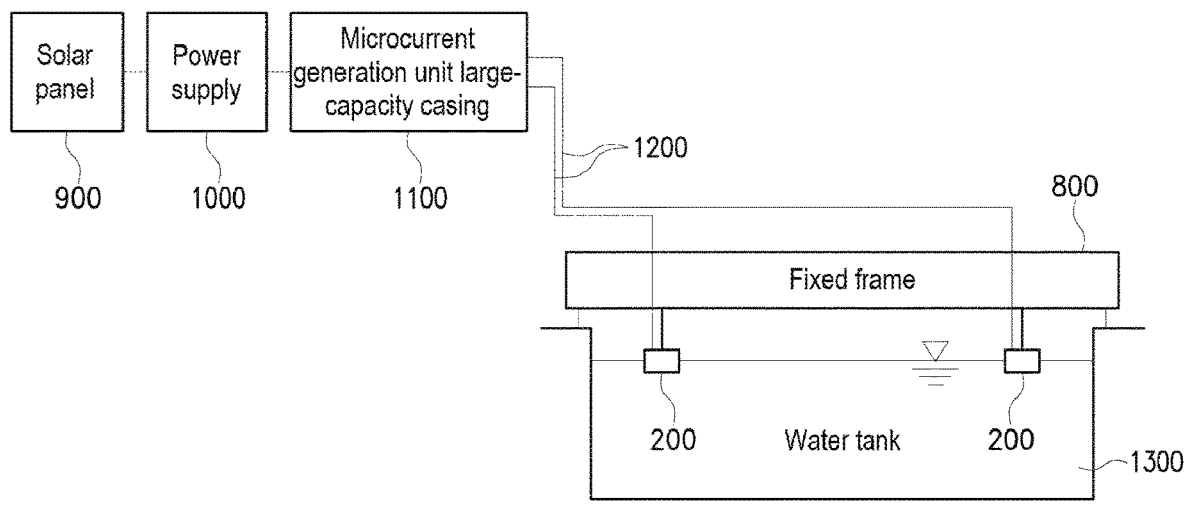
FIG. 9 is a view for showing a superimposed wave microcurrent applying device for living body applied to a fish according to an embodiment of the present invention.

The superimposed wave microcurrent applying device for living body according to the present invention can be applied to fish, and to this end, the superimposed wave microcurrent applying device for living body according to an embodiment of the present invention may be provided with a fixed frame 800, a solar panel 900, a power supply device 1000, a microcurrent generation unit large-capacity casing 1100, and a plurality of connection cables 1200 as shown in FIG. 9.

The fixed frame 800 is disposed in the fish farming area, and at least one or more microcurrent output unit 200 for biostimulation is spaced apart and fixed, and each biostimulation microcurrent output unit 200 is installed to be in contact with the tank 1300 in the fish farming area.

The solar panel 900 is installed at a set point to perform solar power generation.

The power supply device 1000 receives and stores power from the solar panel 900.

The microcurrent generation unit large-capacity casing 1100 is installed at a set point and is connected to the power supply device 1000 and the public power supply to receive power. Since it is connected to a public power supply in preparation for a power outage, it is possible to stably receive power. A plurality of microcurrent generation units 100 for biostimulation are integrated in the microcurrent generation unit large-capacity casing 1100.

The plurality of connection cables 1200 are cables connecting the microcurrent generation unit large-capacity casing 1100 and one or more microcurrent output units 200 for biostimulation.

Figure 10:
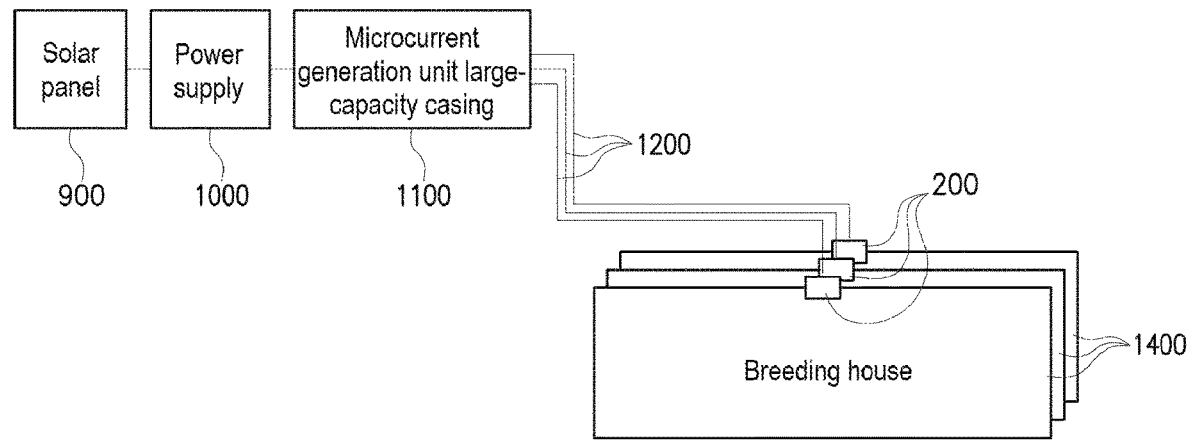
FIG. 10 is a view for showing a superimposed wave microcurrent applying device for living body applied to livestock and poultry according to an embodiment of the present invention.

The superimposed wave microcurrent applying device for living body according to the present invention can be applied to livestock and poultry, and to this end, the superimposed wave microcurrent applying device for living body according to an embodiment of the present invention may be provided with a solar panel 900, a power supply device 1000, a microcurrent generation unit large-capacity casing 1100, and a plurality of connection cables 1200 as shown in FIG. 10.

The solar panel 900 is installed to perform solar power generation at a set point in an animal breeding area where livestock and poultry are reared.

The power supply device 1000 receives and stores power from the solar panel 900.

The microcurrent generation unit large-capacity casing 1100 is installed at a set point and is connected to the power supply device 1000 and the public power supply to receive power. Since it is connected to a public power supply in preparation for a power outage, it is possible to stably receive power. A plurality of microcurrent generation units 100 for biostimulation are integrated in the microcurrent generation unit large-capacity casing 1100.

The plurality of connection cables 1200 are cables connecting the microcurrent generation unit large-capacity casing 1100 and the plurality of microcurrent output units 200 for biostimulation attached to the breeding house 1400 of the animal breeding area.

Here, the feedlot house 1400 is preferably made of a material that conducts electricity or includes a material that conducts electricity.

A superimposed wave microcurrent applying device for living body according to an embodiment of the present invention configured as described above may promote activation of various physiological functions according to the stimulation of the living body since the reference wave microcurrent that can have a very low frequency (VLF) range of 3 to 30 kHz and the main wave micro current that can have a long frequency (LF) range of 30 kHz to 300 kHz are superimposed into a preset pattern, or a superimposed wave microcurrent discretely having a frequency of a larger magnitude sequentially than the main wave microcurrent is additionally superimposed and it is applied to living organisms such as plants, fish, livestock, poultry, humans, animals, and the like. In addition, according to a superimposed wave microcurrent applying device for living body, a reference wave microcurrent and a main wave microcurrent are generated in a way that the trajectory connecting the floor of the wave forming the main wave microcurrent becomes a waveform of the reference wave microcurrent, and since the reference wave microcurrent is generated to have a waveform such as a triangle wave, a square wave, a sawtooth wave, a sine wave, and a DC wave including a staircase wave, there is an effect in that the efficiency of body stimulation for responding to diseases such as pain, cancer, dementia, and viral infection or helping the growth of the human body is to be increased, and meanwhile, to respond to diseases and viral infections of livestock and poultry such as plants grown in vinyl houses, greenhouses, and the like, fish in farms and aquariums, and animals such as cattle, pigs, chickens, ducks, and the like, or to increase the biostimulation efficiency for animal growth activation. In addition, according to a superimposed wave microcurrent applying device for living body according to the present invention, since the micro-current output is driven by a microcurrent output control application installed in a smart watch or smart phone that is integrated or separately disposed with the microcurrent output device, it can be applied to various body parts including the wrist part of the human body in various structures and methods, and accordingly, the usability and expandability can be increased. In addition, the superimposed wave microcurrent applying device for living body according to the present invention, since after disease of a user is estimated by detecting image information of a body area, iris characteristic information, vein characteristic information, and the like by a smart watch or smartphone, and then a structure in which a microcurrent tailored to this is generated and outputted is provided, so activation of physiological functions optimized for the current state of the user can be implemented.

As described above, a superimposed wave microcurrent applying device for living body according to an embodiment of the present invention is illustrated in accordance with the above description and drawings, but this is only described as an example and it will be well understood by those of ordinary skill in the art that various changes and modifications are possible within the scope not departing from the technical idea of the present invention.

The invention claimed is:

1. A superimposed wave microcurrent applying device for living body, comprising:
  a microcurrent generation unit for biostimulation that generates a biostimulation microcurrent in which a reference wave microcurrent and a main wave microcurrent are superimposed;
  a microcurrent output unit for biostimulation connected to the microcurrent generation unit for biostimulation to receive the biostimulation microcurrent and outputs the biostimulation microcurrent to an external area to stimulate a subject live body in the external area;
  a controller that controls the operation of the microcurrent generation unit for biostimulation and the microcurrent output unit for biostimulation, wherein the microcurrent generation unit generates a reference wave microcurrent having a frequency belonging to a reference wave frequency range set as a very low frequency (VLF) wave of 3 to 30 kHz and a current value within a preset microcurrent value range for biostimulation, the reference wave microcurrent haing any one waveform selected from a DC wave group including a triangular wave, a square wave, a sawtooth wave, a sine wave, and a step wave, wherein the microcurrent generation unit comprises:
  a reference wave microcurrent generation module that generates only in a region having a positive wave displacement value;
  a main wave microcurrent generation module that generates a frequency within a main wave microcurrent frequency range set to a long wave (LF) of 30 kHz to 300 kHz, which is greater than the frequency of the reference wave micro current, and a main wave microcurrent with a current value that falls within the set biostimulation microcurrent value range; and
  a microcurrent superimposing module that superimposes the reference wave microcurrent and the main wave microcurrent;
  a housing that is wearable on a human body;
  a main board disposed inside the housing and on which the microcurrent generation unit for biostimulation, the microcurrent output unit for biostimulation, and the controller are mounted in a chipset form;
  a control panel that is formed to be exposed on the surface of the housing, receives a control signal according to a user's manipulation and transmits it to the controller, and receives and outputs information from the controller;
  a watch-type main body block made of a block body shape having a preset thickness corresponding to the shape of a main watch body, and a center portion of the bottom surface in contact with the living body consists of an AC electric stimulation plate; and
  a connection band connected to both sides of the watch-type main body block and fixable to the wrist area of a human body, wherein the AC electric stimulation plate is connected to the microcurrent output unit for biostimulation to receive the microcurrent for biostimulation;
  wherein the main wave microcurrent generation module generates a main wave microcurrent of the waveform that satisfies all of a first condition in which the wave displacement value of the main wave microcurrent for each time does not exceed the wave displacement value of the reference wave microcurrent at a corresponding time, and a second condition in which the wave displacement value of the main wave microcurrent by time and the wave displacement value of the reference wave microcurrent at a corresponding time are the same, and at the same time, generates a main wave microcurrent so that a trajectory connecting the floor of the wave constituting the main wave microcurrent becomes a waveform of the reference wave microcurrent.

2. The superimposed wave microcurrent applying device for living body according to claim 1, wherein the watch-type body block of the housing additionally forms a DC electric stimulation electrode at the edge of the bottom surface in contact with a living body, and the DC electric stimulation electrode is connected to a DC power generator disposed inside the housing to receive a DC current for biostimulation.

3. The superimposed wave microcurrent applying device for living body according to claim 1, wherein the connection band is attached with a biostimulatory mineral body including germanium and crystal in an area to be in contact with a living body.

4. The superimposed wave microcurrent applying device for living body according to claim 1, comprising any one or more selected from the group of:
  a microcurrent output terminal provided with the microcurrent generation unit for biostimulation and the microcurrent output unit for biostimulation;
  a smart watch made in the shape of a wristwatch, wearable on the user's wrist, and equipped with the controller, and a first database memory in which the microcurrent setting information for generating the microcurrent for the biostimulation is databased;

a user portable communication terminal, carried by a user for mobile communication, installed with a microcurrent output control application interlocked with the controller, wherein the microcurrent output control application includes a second database memory in which the microcurrent setting information for generating the microcurrent for the biostimulation is databased, wherein the smart watch is any one selected from: an output terminal integrated smart watch in which the smart watch and the microcurrent output terminal are integrated, and the controller is built-in to perform direct control of the microcurrent output terminal;

and a detachable smart watch separately provided from the microcurrent output terminal, and provided with a communication unit, thereby transferring an output terminal operation control information to the microcurrent output terminal through wired or wireless communication with the microcurrent output terminal, and wherein the user portable communication terminal is any one selected from:

an indirect control communication terminal indirectly controlling the microcurrent output terminal by transmitting the output terminal operation control information generated from the microcurrent output control application to the smart watch through wireless communication with the smart watch;

and a direct control communication terminal directly controlling the microcurrent output terminal by transmitting the output terminal operation control information generated from the microcurrent output control application to the microcurrent output terminal through wireless communication with the microcurrent output terminal to the microcurrent output terminal.

5. The superimposed wave microcurrent applying device for living body according to claim 4, wherein the output terminal integrated smart watch has a structure in which the smart watch and the microcurrent output terminal are detachably coupled, and in case of outputting a microcurrent for biostimulation to a living body area other than the wrist of a user, the microcurrent output terminal is separated from the smart watch and can be placed in a corresponding living body area.

6. The superimposed wave microcurrent applying device for living body according to claim 4, wherein the microcurrent output terminal can deliver microcurrent for biostimulation by being connected with one or more of:
 a wearable object for a user including a small sound device worn on the ear, glasses worn on the eyes, and a hat worn on the head; an object in contact with user's body including a bed, a bed pad, and an electric pad.

7. The superimposed wave microcurrent applying device for living body according to claim 4, wherein the microcurrent output terminal is configured to be disposed on an area of a living body to detect current body information of a user, and any one selected from the smart watch and the user portable communication terminal receive current body information of the user from the microcurrent output terminal and generate and output monitoring information.

8. The superimposed wave microcurrent applying device for living body according to claim 4, further comprising:
 a solar cell disposed on the surface of the smart watch to generate power by receiving sunlight;
 a body temperature charging unit that generates power from body temperature transmitted from the wrist where the smart watch is disposed;
 a wireless wave charging unit for producing power from wireless waves including radio waves for Wi-Fi communication, radio waves for Bluetooth communication, and radio waves for LTE communication received by the smart watch;
 and a vibration charging unit for generating power from shaking motion of the smart watch is provided in the smart watch.

9. The superimposed wave microcurrent applying device for living body according to claim 4, wherein any one selected from the smart watch and the user portable communication terminal is provided with any one or more selected among a group consisting of:
 a body image information detector for generating image information of a body part used for disease diagnosis;
 an iris recognition sensor for detecting iris characteristic information of a user;
 a vein recognition sensor for detecting vein characteristic information of a user, wherein any one selected from a human body diagnosis unit provided in the smart watch and the microcurrent output control application provided in the user portable communication terminal estimates disease of a user from information inputted from any one or more selected among a group consists of the body image information detector, the iris recognition sensor, and the vein recognition sensor, and wherein the smart watch and the microcurrent output control application receive microcurrent setting information corresponding to the estimated disease of a user from the first and/or second database memory, generate output terminal operation control information, and then the microcurrent setting information is transmitted to the microcurrent output terminal.

* * * * *